United States Patent
Yun et al.

(10) Patent No.: US 7,414,787 B2
(45) Date of Patent: Aug. 19, 2008

(54) PHASE CONTRAST MICROSCOPE FOR SHORT WAVELENGTH RADIATION AND IMAGING METHOD

(75) Inventors: Wenbing Yun, Walnut Creek, CA (US); Yuxin Wang, Arlington Heights, IL (US)

(73) Assignee: Xradia, Inc., Concord, CA (US)

( * ) Notice: Subject to any disclaimer, the term of this patent is extended or adjusted under 35 U.S.C. 154(b) by 0 days.

(21) Appl. No.: 11/468,986

(22) Filed: Aug. 31, 2006

(65) Prior Publication Data

US 2007/0002215 A1   Jan. 4, 2007

Related U.S. Application Data

(62) Division of application No. 10/331,108, filed on Dec. 27, 2002, now Pat. No. 7,119,953.

(51) Int. Cl.
*G02B 27/44* (2006.01)
(52) U.S. Cl. ............... 359/565; 359/900; 359/742; 257/797; 438/975
(58) Field of Classification Search ............... None
See application file for complete search history.

(56) References Cited

U.S. PATENT DOCUMENTS

| | | | |
|---|---|---|---|
| 3,628,848 A | 12/1971 | Nomarski | |
| 3,637,280 A | 1/1972 | Beyer et al. | |
| 3,728,009 A | 4/1973 | Fedotowsky et al. | |
| 4,798,446 A | 1/1989 | Hettrick | |
| 4,870,674 A | 9/1989 | Schmahl et al. | |
| 4,953,188 A | 8/1990 | Siegel et al. | |
| 5,144,483 A | 9/1992 | Cohen | |
| 5,199,057 A | 3/1993 | Tamura et al. | |
| 5,222,113 A | 6/1993 | Thieme et al. | |
| 5,257,132 A | 10/1993 | Ceglio et al. | |
| 5,550,887 A | 8/1996 | Schmal et al. | |
| 5,615,199 A | 3/1997 | Tatsuno et al. | |
| 5,708,526 A | 1/1998 | Stankewitz | |
| 5,715,091 A | 2/1998 | Meyers | |
| 5,814,815 A | 9/1998 | Matsumoto et al. | |

(Continued)

FOREIGN PATENT DOCUMENTS

EP   1 006 400 A2   6/2000

(Continued)

OTHER PUBLICATIONS

Di Fabrizio, Enzo, et al., "Nano-optical elements fabricated by e-beam and x-ray lithography," Proceedings of SPIE, vol. 5225 Nano- and Micro-Optics for Information Systems, edited by Louay A. Eldada, (SPIE, Bellingham, WA, 2003) pp. 113-125.

*Primary Examiner*—Arnel C Lavarias
(74) *Attorney, Agent, or Firm*—Houston Eliseeva LLP

(57) ABSTRACT

A phase contrast x-ray microscope has a phase plate that is placed in proximity of and attached rigidly to the objective to form a composite optic. This enables easier initial and long-term maintenance of alignment of the microscope. In one example, they are fabricated on the same high-transmissive substrate. The use of this composite optic allows for lithographic-based alignment that will not change over the life-time of the instrument. Also, in one configuration, the phase plate is located between the test object and the objective.

17 Claims, 7 Drawing Sheets

U.S. PATENT DOCUMENTS

| | | |
|---|---|---|
| 6,167,112 A | 12/2000 | Schneider |
| 6,269,145 B1 * | 7/2001 | Piestrup et al. ............... 378/81 |
| 6,389,101 B1 | 5/2002 | Levine et al. |
| 6,449,095 B1 | 9/2002 | Ohtaki et al. |
| 6,744,048 B2 | 6/2004 | Hosokawa et al. |

FOREIGN PATENT DOCUMENTS

| | | |
|---|---|---|
| JP | 1-128000 | 5/1989 |
| WO | 01/65305 A1 | 9/2001 |

* cited by examiner

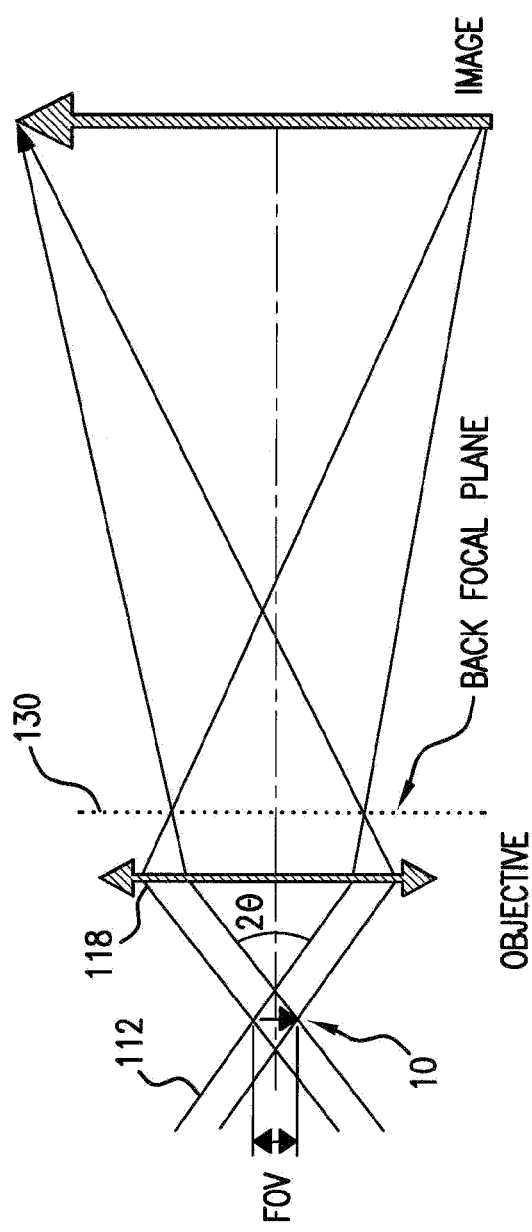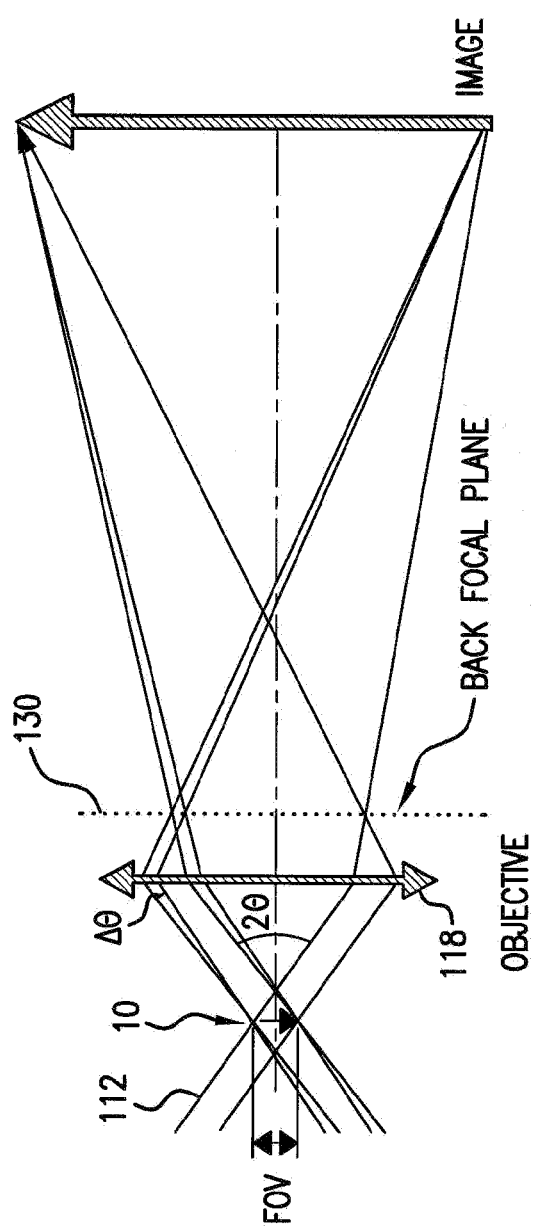

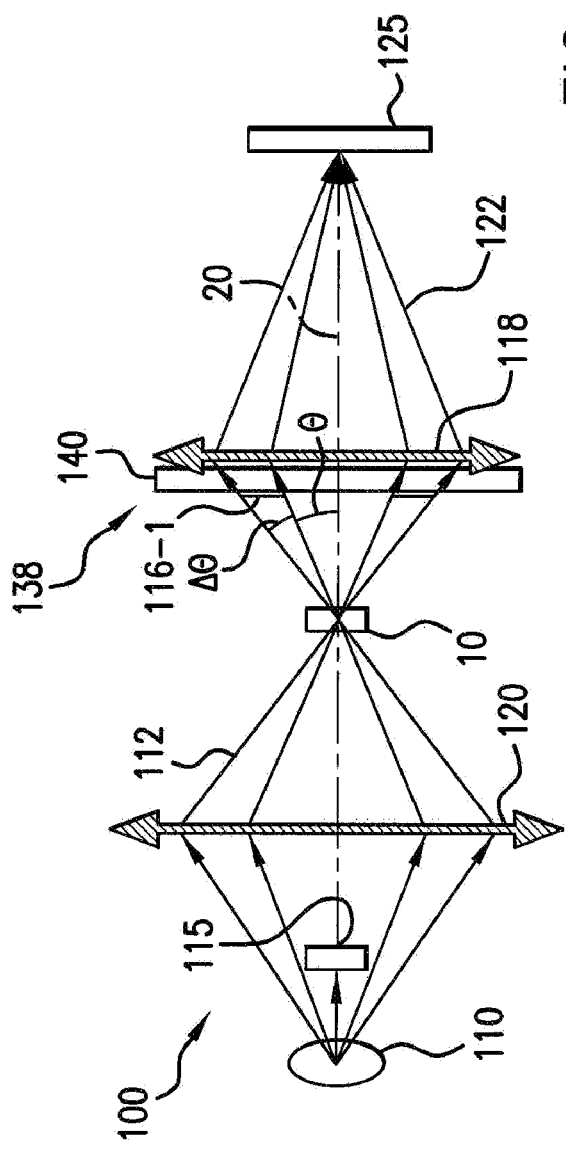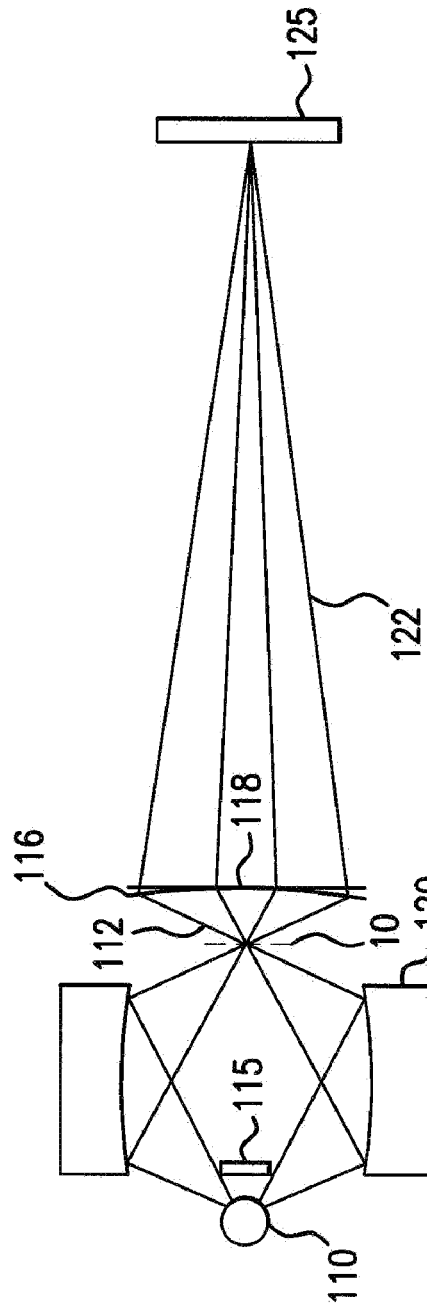

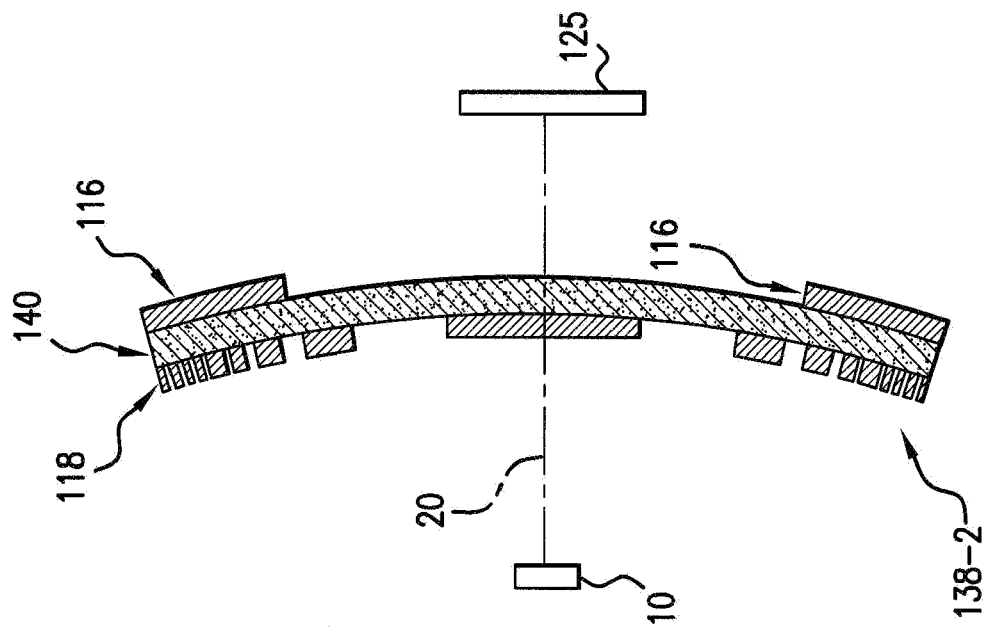
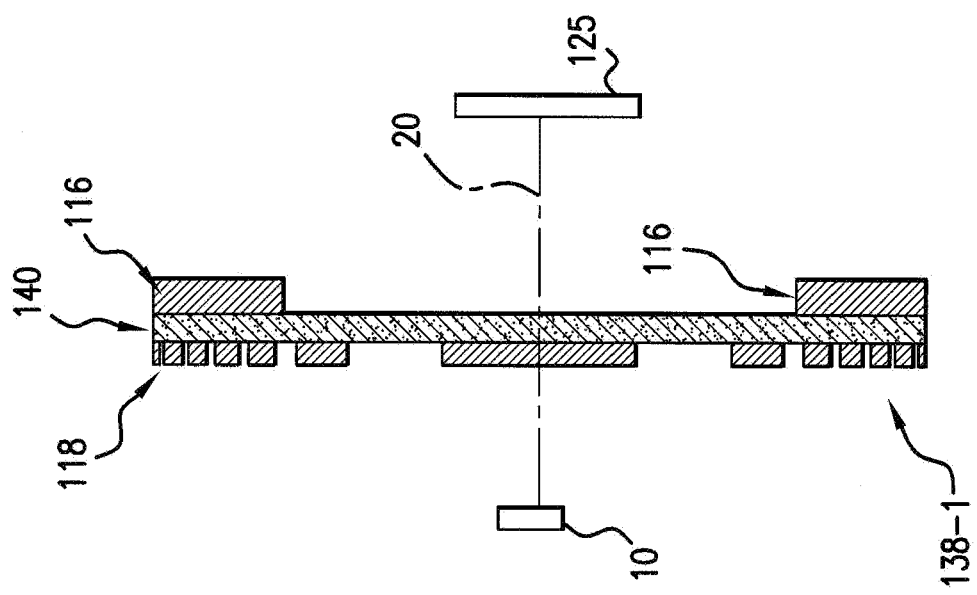

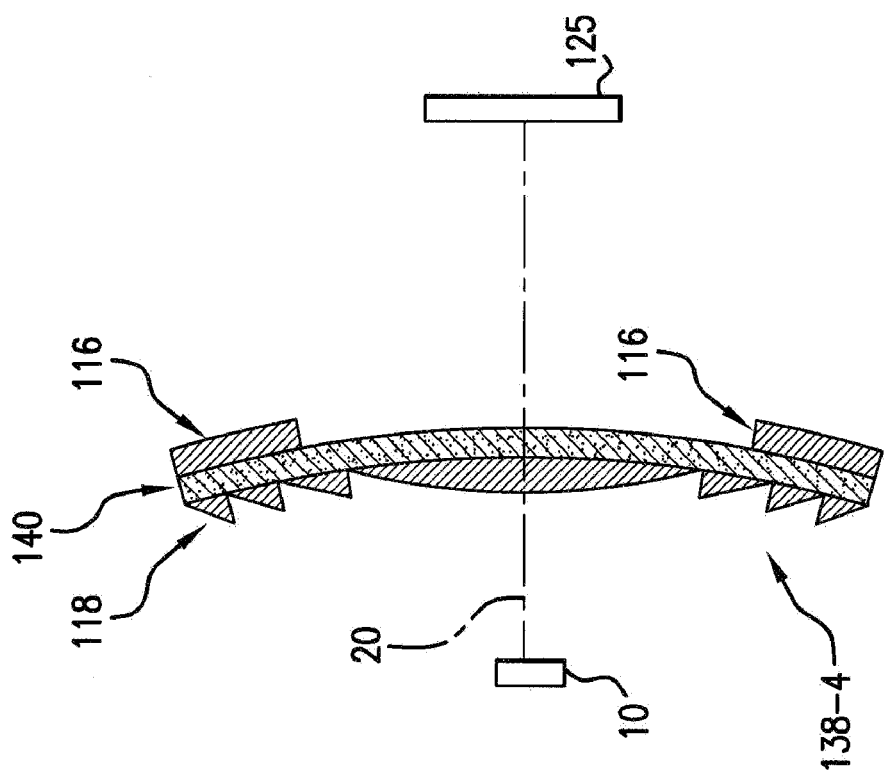
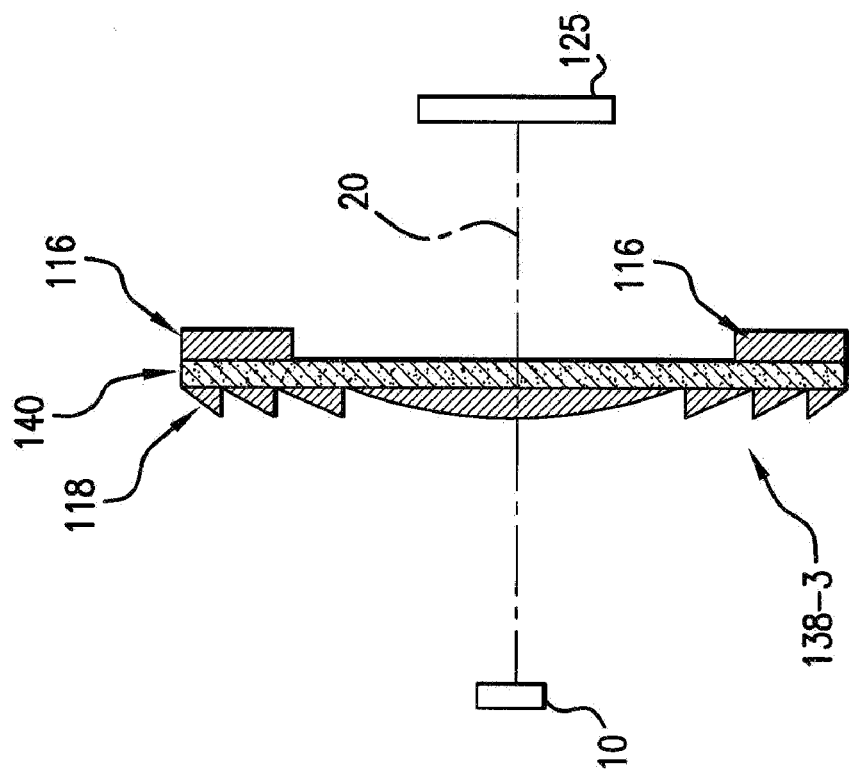
FIG. 4A
FIG. 4B

PHASE CONTRAST MICROSCOPE FOR SHORT WAVELENGTH RADIATION AND IMAGING METHOD

RELATED APPLICATIONS

This application is a Division of U.S. application Ser. No. 10/331,108, filed Dec. 27, 2002, now U.S. Publication Number US 2004/0125442 A1, published on Jul. 1, 2004, which is incorporated herein by reference in its entirety.

BACKGROUND OF THE INVENTION

Short wavelength microscopes are devices that produce a magnified image of an object utilizing electromagnetic radiation in the extreme ultraviolet (EUV) and x-ray regime. The wavelengths range from 20 nanometers (nm) to 0.02 nm. These microscopes typically develop image contrast by relying on photoelectric absorption in the test object. Different elements, or structures formed of elements, attenuate the x-rays to varying degrees.

In a typical short wavelength microscope configuration, a focusing element, such as a condenser, is used to concentrate the radiation on the test object. An objective, such as a zone plate, collects the radiation after transmission through the object and forms an image on a detector, such as a charge-coupled device or film. Intervening scintillators are sometimes required, depending on the specific wavelength and detector used.

Absorption-based x-ray microscopy, however, tends to impose certain limitations on the types of structures that can be imaged. Generally, absorption contrast decreases in proportion to the third power of the photon energy of the radiation. This tends to motivate for the use of lower energies, but lower energies may not provide sufficient penetration through the object.

Moreover, absorption-based x-ray microscopy may also fail to provide sufficient contrast between structures within the object of interest when those structures are composed of elements that have similar atomic numbers. Absorption contrast is generally proportional to the fourth power of the atomic number, away from an absorption edge. Absorption contrast x-ray microscopy therefore works well when imaging structures consisting of mostly high atomic number elements, such as gold or tungsten, in a host material consisting of mostly low atomic number elements, such as silicon. It is generally difficult, however, to use absorption contrast to image small structures consisting of mostly low atomic number elements in a test object containing non-negligible amounts of high atomic number elements, such as imaging cracks in dielectrics of a multilevel integrated device.

An alternative to absorption contrast x-ray microscopy is sometimes termed phase contrast x-ray microscopy. Here, the phase shifting properties of the structures within the object of interest are used to create the image contrast between the structures. To utilize the phase contrast, a phase shifting element is typically placed at the back focal plane of the objective to impart a suitable phase shift to the direct beam, i.e., radiation that passed directly through the test object. The focal plane is the plane parallel to the lens that passes through the point at which parallel rays of light meet after being focused by the lens. The phase shifted direct beam interferes at the image plane with radiation that was scattered and diffracted in the test object. Thus, contrast is produced in response to the phase shifting properties or refractive indices of structures within the test object.

Phase contrast x-ray microscopy has some intrinsic characteristics that render it more effective in many types of imaging applications. First, phase contrast is generally significantly larger than absorption contrast in the 0.02-20 nanometer (nm), short wavelength spectral region. As a consequence, exposure time can be substantially reduced. Secondly, phase contrast is inversely proportional to the energy except for a narrow spectrum near an absorption edge. As a result, doubling the energy decreases the phase contrast only by a factor of two while the penetration power increases by a factor of eight. This allows for thicker samples, easing the requirements for sample preparation, or allows for the imaging of samples nondestructively. Moreover, phase contrast between elements is roughly related to the mass density, rather than the atomic number, except for a narrow spectrum near an absorption edge. This enables the imaging of structures comprising low atomic numbered elements alone or in a host materials matrix containing high atomic number elements. It is especially applicable to imaging structures comprising organic compounds, silicon, and/or oxygen, for example.

In the past, the optical trains of phase contrast x-ray microscopes were similar to the trains used for optical frequencies. In a conventional configuration, the scattered light was phase shifted relative to the direct beam by, typically, 90 degrees with a quarter wave plate or 270 degrees with a three quarter wave plate that was located at the back focal plane of the objective to retard or advance the phase of the direct beam. There was typically a requirement to attenuate the direct beam so that it had comparable intensity as the collected, scattered signal radiation. This provided higher contrast because complete extinction occurred during destructive interference when the two interfering beams are of the same amplitude.

SUMMARY OF THE INVENTION

One challenge that arises in the operation of these conventional phase contrast microscopes is achieving and maintaining alignment between the objective and the phase plate. The objective and the phase plate must be aligned in the two axes that are perpendicular to the optical axis of the microscope. In some implementations, the elements must be aligned to better than about 0.5 to 1 micrometers for short wavelength microscopes using x-rays, for example. Also, there are typically minimum tolerances for angular alignments between these two optical elements and the surrounding optical train.

In the prior art devices, this alignment has been difficult to achieve during the initial assembly of the microscope and to maintain the alignment over the microscope's lifetime, because the distance between the phase plate and the objective is substantially larger than the alignment tolerance. Misalignment induced by thermal drift or mechanical vibration, for example, can render the alignment dynamic over an exposure and lead to performance degradation over time.

According to the present invention, the phase plate is placed away from the objective's back focal plane and preferably in close proximity to the objective, instead of at the back focal plane of the objective as in the prior art. The close proximity facilitates the initial alignment between the zone plate and the phase plate, and the maintenance of that alignment over time. In one example, the zone and phase plates are fabricated on the same substrate or mounted rigidly together, producing a composite optical device, resulting in accurate alignment over a long period of time. The present invention limits the field of view to be a fraction of the entrance pupil of the objective but this limitation is acceptable for many practical applications, especially in the short wavelengths.

In general, the invention features a phase contrast x-ray microscope, which comprises a source for irradiating a test object with short wavelength irradiation and a detector for detecting the radiation from the test object. An objective images and magnifies the radiation from the object onto the detector, with the direct beam (undiffracted beam by the object) suitably phase shifted by a phase plate. A field aperture defines an appropriate field of view for imaging.

According to a preferred embodiment of the invention, a phase plate and the objective are rigidly attached at a close proximity by, for example, fabricating on or mounting them to the same substrate.

In the typical implementation, a condenser is used to relay the radiation from the source to the test object. A reflective optic, such as a capillary or Wolter optics, or a diffractive condenser zone plate, is used in the current implementation.

In the current embodiment, the objective comprises a zone plate lens.

In an alternative embodiment, the objective comprises a Fresnel optic. In yet another alternative embodiment, the objective comprises a Wolter optic.

Depending on the implementation, the radiation can be detected, for example, using standard silver-based film or electronically using a detector array, such as a charged coupled device (CCD).

In general, according to another aspect, the invention also features a composite optic for a phase contrast x-ray microscope. This optic comprises a substrate and a lens attached to the substrate. A phase plate is also attached to this same substrate.

According to still another aspect, the invention features a method for imaging structures of a test object. The process comprises configuring an optical train including an objective, having a back focal plane, and a phase plate, which is located in the optical train away from the back focal plane of the objective. The test object is irradiated with short wavelength radiation. A differential phase shift is induced between direct radiation and diffracted radiation from the test object with the phase plate. The radiation is imaged onto a detector with the objective.

In general, according to still another aspect, the invention features a method for fabricating a composite optic. It comprises forming fiducials on a substrate. An objective and a phase plate are also formed on the substrate. The phase plate is aligned relative to the objective using the fiducials.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIGS. 1A and 1B are schematic views of optical trains of a phase contrast microscope illustrating why the phase plate 116 (not shown in figure) is placed at the back focal plane 130 of the objective 118 in prior art implementations and the validity conditions for the implementation of phase contrast imaging according to the present invention;

FIG. 2A is a schematic view of an optical train of a phase contrast x-ray microscope according to the present invention;

FIG. 2B is a schematic view of an optical train of a phase contrast x-ray microscope according to a current implementation of the present invention;

FIGS. 3A and 3B are cross-sectional views of composite optics comprising zone plates that are formed on one side of a substrate and phase rings that are formed on the other side of the substrate, according to the present invention;

FIGS. 4A and 4B are cross-sectional views of inventive composite optics comprising a Fresnel lens that is formed on one side of a substrate and the phase ring that is formed on the other side of the substrate;

DETAILED DESCRIPTION OF THE PREFERRED EMBODIMENTS

Figures 5A, 5B:
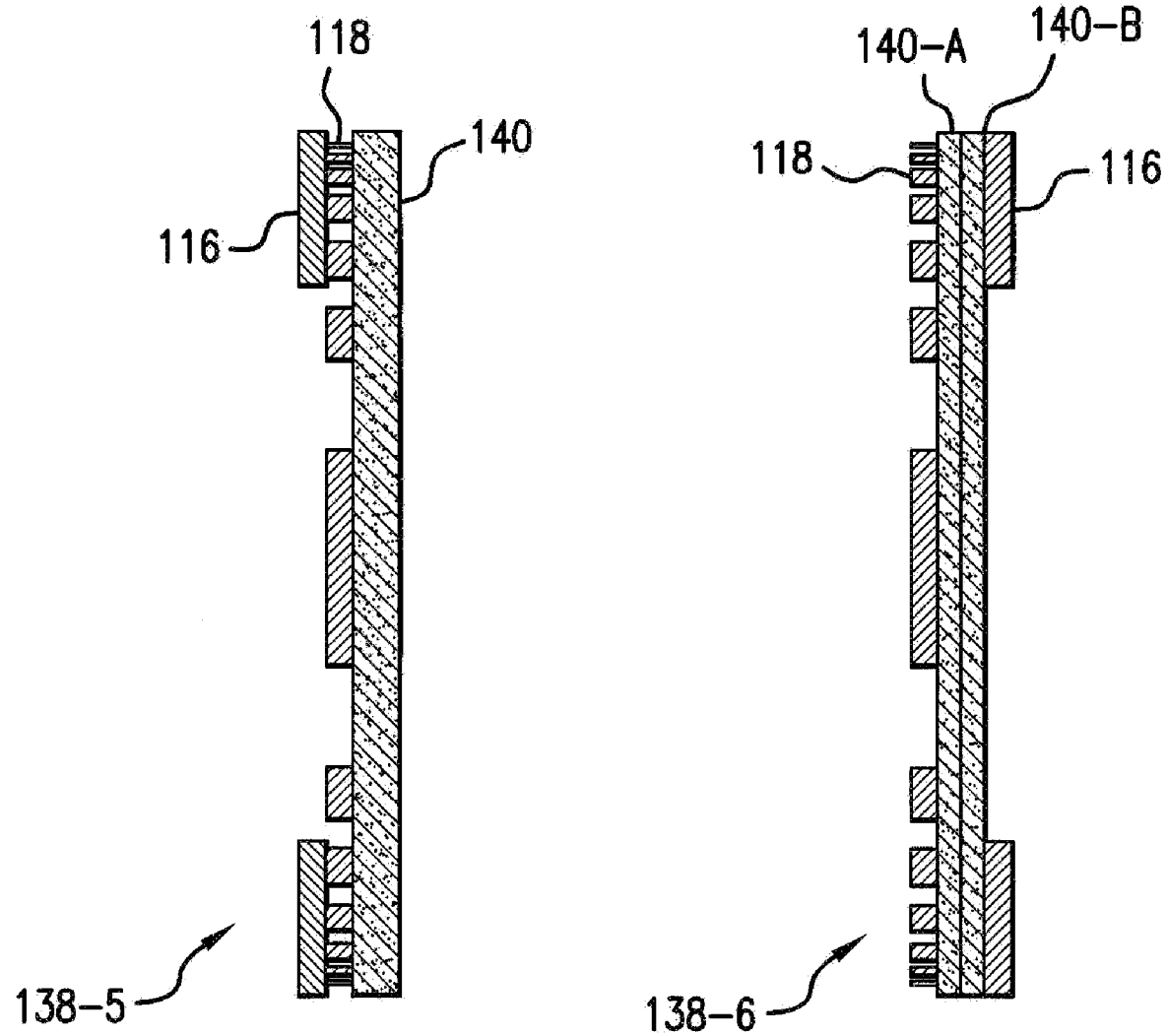
FIGS. 5A and 5B are cross-sectional views of composite optics comprising zone plates and phase plates according to still other embodiments.

FIGS. 1A and 1B schematically illustrate why phase plates are placed at the back focal planes of objectives in the typical phase contrast microscope configuration and the validity conditions for the phase contrast imaging configuration according to the present invention.

Four important parameters characterize the illumination beam 112: 1) the brightness B, 2) the field of view (FOV), 3) the mean numerical aperture $NA_c = \sin \theta$, and 4) the angular spread $\Delta\theta$.

The photon flux incident on the test object 10 within the field of view (FOV) is proportional to $B*2\pi*(1-\cos \theta)$, which approximately equals to $(B*2\pi*\sin \theta*\Delta\theta)$ for small $\theta$. The exposure time is inversely proportional to this photon flux.

The brightness B is typically constrained by the device used. The source brightness and the throughput of the optical system relaying the photons from the source to the test object 10 to thus produce the illumination beam 112 dictate the level of the brightness.

Thus, for a given brightness, it is important to maximize the $\sin \theta*\Delta\theta$ product to reduce exposure time, for example. In general, the mean numerical aperture $NA_c$ is equal to or smaller than the numerical aperture NA of the objective 118. In order to reduce exposure time, one consequently needs to increase $\Delta\theta$. There are consequences, however, to increasing $\Delta\theta$ on the imaging property of the phase contrast microscope, which must be considered, however.

FIG. 1A schematically shows that the width of the phase ring required at the back focal plane 130 is very narrow for a very small $\Delta\theta$.

FIG. 1B shows that the width of the phase ring required at the back focal plane 130 is finite when $\Delta\theta$ is a finite yet still small. Generally, the width of the phase ring is approximately equal to $f*\Delta\theta$, where f is the focal length of the objective 118.

Because of the finite phase ring width required for small $\Delta\theta$ in combination with the intended phase shift for the direct beam, the low spatial frequency component of the beam diffracted by the test object 10 will also be unintentionally phase shifted. This unintentional phase shift results in the so-called "halo-effect" at edges of images corresponding to large features. Thus, for a given $\Delta\theta$, the minimum feature size that may have "halo-effect" is approximately equal to $2\lambda/\Delta\theta$, where $\lambda$ is the average wavelength of the illumination beam.

The "halo effect" is acceptable in most practical phase contrast microscopes and what is the acceptable minimum feature size is often an important consideration in designing a phase contrast microscope.

FIG. 1B shows that when the FOV is substantially small, the phase ring width at the back focal plane 130 is approximately equal to its projected width on the objective 118, especially when the NA of the objective is large. The present invention recognizes that in this case the phase ring can be placed away from the back focal plane 130 of the objective 118 and in proximity to the objective 118, for example, without affecting the imaging property of the phase contrast microscope. The acceptable FOV may be defined by FOV<O*$\Delta\theta$, where O is the distance between the test object 10 and the objective 118.

FIG. 2A shows an optical train for a phase contrast short wavelength microscope, which has been constructed according to the principles of the present invention. It preferably utilizes electromagnetic radiation in the extreme ultraviolet (EUV) and x-ray regime, between about 20 nanometers (nm) to 0.02 nm in the present embodiment.

Specifically, the optical train 100 comprises a source 110. In one example, the primary X-ray radiation is generated by bombarding a solid target with energetic electrons, or by focusing a sufficiently intense laser beam on a solid or liquid target to generate plasma of a sufficiently high temperature. A synchrotron can also be used.

A condenser 120 is used to collect and relay the radiation from the source 110 to the test object 10. The condenser 120 preferably performs three functions: increasing the flux density of the illumination beam 112 at the test object 10 to speed the image collection time, increasing resolution of the microscope by delivering the illumination beam 112 with an appropriate numerical aperture, and shaping the illumination beam 112 with a suitable angular spread $\Delta\theta$ in conjunction with a suitably shaped aperture 115. In one example, a capillary optic condenser with a suitably configured reflecting surface is used. For example, the reflecting surface is usually an ellipsoid reflecting surface to form an image of the source 110 on the test object 10. Single layer or multilayer coatings are preferably used to increase reflection efficiency. In another example, a Wolter optic with suitable optical parameters is used. A reflecting surface of the Wolter optic comprises a single layer or a multilayer coating to increase reflection efficiency. In yet another example, the condenser 120 is a zone plate.

The beam 112 from the condenser 120 is generally conically shaped. An aperture 115 is typically used to render this beam hollow to form a hollow cone illuminating beam. That is, substantially no radiation is present that is directed along or at small angles to the optical axis 20. Depending on the implementation, the aperture 115 is placed before, after, or in the condenser 120.

According to the present invention, the area of the illumination beam projected on the entrance pupil plane is typically a fraction of the area of the objective pupil, i.e., the illumination beam 112 incident on the objective 118 occupies a small fraction of the surface of the objective 118. This fraction is typically limited to less than 0.2. It is typically between 0.01 and 0.2.

The converging, hollow beam 112 irradiates the test object 10. Different structures within the test object 10 are comprised of different constituent elements with different refractive indices and therefore phase shifting properties. The patterns of these structures in the plane that is orthogonal to the optical axis 20 further have different spatial frequencies. As a result, the radiation tends to be scattered and diffracted out of the path of the direct radiation beam occupying angle $\Delta\theta$ and the diffracted radiation covering a larger cone is partially or completely collected by the objective 118 and delivered to the image plane to produce an image.

The exiting radiation from the test object 10 including both the direct beam and the diffracted radiation passes through a phase plate 116. In the illustrated example, the phase plate 116-1 is implemented as a phase ring to induce a phase shift between the radiation of the direct beam in angle $\Delta\theta$ and the radiation diffracted from the object 10 and collected by the objective 118 but not passing through the phase plate 116. Specifically, in the typical implementation, material and thickness of the phase plate 116-1 are selected to induce a relative 90 or 270 degree phase retardation between the diffracted radiation and the direct beam radiation to produce a positive phase contrast or negative phase contrast. Sometimes, this relative phase change is more than 270 degrees and is equal to substantially a product of 90 degree with an odd integer, such as 5, 7, 9, etc. The ring 116 has a uniform thickness and extends parallel to the objective 118.

In the preferred embodiment, the material of the phase ring 116-1 in the path of the direct radiation is selected to achieve a desired attenuation to improve image contrast by balancing the relative strength of the interfering diffracted and direct beams because, typically, the direct beam radiation is much more intense that the scattered radiation.

After the selective phase shifting, the radiation passes through an objective 118. This objective 118 forms an image on a detector 125 by creating the focused radiation 122. In the preferred embodiment, the objective 118 is a zone plate lens, a Wolter optic, or a Fresnel optic.

In an alternative embodiment, the phase plate 116-1 is placed after the objective 118 in the optical train. The critical notion is that the phase plate 116-1 is moved away from the back focal plane of the objective 118 and preferable nearer to the objective 118 in order to improve the alignment between the objective 118 and the phase plate 116-1.

According to one aspect of the invention, the phase plate 116 and the objective 118 are attached to and preferably fabricated on the same high-transmissive substrate 140 to form a composite optic 138. In one example, the high-transmissive substrate 140 is a low stress $Si_3N_4$ membrane of a thickness between 100-1000 nm. The high-transmissive substrate 140 is more than 80%, transmissive to the radiation of the illumination beam 112 in most implementations, and is preferably greater than 95% transmissive in the preferred embodiment. The objective 118 and the phase plate are fabricated by patterning a resist material that has been deposited on the high-transmissive substrate 140, and then plating into the patterned resist and onto the silicon wafer.

An important advantage of having the phase plate 116 and the objective 118 attached to a common high-transmissive substrate 140 is achieving and maintaining alignment. The two optical elements are aligned to lithographic accuracies in the situation where they are fabricated on the same high-transmissive substrate. In the situation in which they are mechanically attached to a common high-transmissive substrate, the phase plate 116 and the objective 118 are fabricated on separate high-transmissive substrates, which are then attached to each other. In this implementation, standard wafer-to-wafer alignment and bonding techniques are used.

In the preferred embodiment, the detector 125 is a detector array, such as a charged couple device (CCD) array. Alternatively, a film-based detection is implemented. Further, in other implementations, a scintillator may be necessary, depending on the wavelength of radiation and the bandwidth of the detector 125.

FIG. 2B shows a current implementation of the optical train for the phase contrast short wavelength microscope. It shows the preferred capillary optic condenser 120. It further shows the general arrangement in which the distance between the test object 10 and the objective 118 is much shorter than the objective 118 and the detector 125 to obtain a magnified image. Typically, distances are about 1-200 millimeters (mm) for the object distance, i.e., the distance between the test object 10 and the objective 118, and 100-3000 mm for the image distance, i.e., the distance between the objective 118 and the detector 125.

FIGS. 3A and 3B show two related implementations of a composite optic 138, which have been constructed according to the principles of the present invention.

With reference to FIG. 3A, the phase ring 116 and a zone plate objective 118 are fabricated on a common high-transmissive substrate 140. Specifically, the zone plate 118 is formed on one side of high-transmissive substrate 140 and the phase ring 116 is formed on the other side of the high-transmissive substrate 140, in the illustrated example.

It should be noted that this composite optic 138-1 could be oriented in either direction in optical path between the test object 10 and the detector 125. In one embodiment, the phase ring 116 is located between the zone plate objective 118 and the test object 10. Alternatively, as shown, the composite optic 138 is oriented such that the zone plate objective 118 is between the test object 10 and the phase plate 116.

Because the objective 118 and the phase plate 116 are formed on the same high-transmissive substrate 140, a single positional and angular alignment of the high-transmissive substrate 140 is required to the optical axis 20 of the optical train 100.

In a second implementation of FIG. 3B, the high-transmissive substrate 140 of composite optic 138-2 is fabricated to have a curve. Preferably, this curve is spherical, with the curve being in the direction of the test object 10. This minimizes changes in the angle of incidence across the phase plate 116. This curvature can be induced by using a flexible high-transmissive substrate 140 and controlling the stress properties of the material deposited on the high-transmissive substrate 140.

FIGS. 4A and 4B illustrate other embodiments of the composite optic 138 that have Fresnel-lens type objectives, as illustrated, or achromatic Fresnel optic objectives.

With reference to FIG. 4A, the objective 118 is configured as a Fresnel lens. It is formed on a common high-transmissive substrate 140 with the phase ring 116 to form composite optic 138-3. In the illustrated optical train 100, the composite optic 138-3 is oriented such that the Fresnel objective 118 is between the phase plate 116 and the test object 10. However, in other implementations, this composite optic 138-3 can be flipped so that the phase plate 116 is adjacent to the test object 10.

As illustrated in FIG. 4B, in some embodiments, the high-transmissive substrate 140 of composite optic 138-4 is fabricated with an arcuate, or specifically spherical shape, curving in the direction of the test object 10. In this embodiment, the Fresnel lens objective 116 is fabricated on the side of the high-transmissive substrate 140 adjacent the test object 10, or the concave side. In other implementations, the phase plate 118 is fabricated on side of the high-transmissive substrate 140 adjacent the test object 10, or the concave side.

It should be noted that, although in the previous embodiments, the phase plate 116 and the objective 118 have been shown to be fabricated on opposite sides of the high-transmissive substrate, in other embodiments, they are fabricated on the same side, using a two-step patterning and plating process.

This arrangement is shown in FIG. 5A. Specifically, the phase plate 116 is shown as being fabricated over the zone plate objective 118, which in turn is fabricated on the high-transmissive substrate 140 to form the composite optic 138-5. This configuration is deemed preferable since the yields associated with the fabrication of the zone plate 118 are typically lower than the phase plate 116, thereby improving overall yields when the zone plate 118 is fabricated first. Further, a planarizing filler is usually coated over the zone plate 118 before the phase plate 116 is fabricated on the zone plate 118.

As shown in FIG. 5B, in still another embodiment, the composite optic 138-6 is fabricated by fabricating each of the zone plate 116 and the phase plate 118 on separate high-transmissive substrates 140-A and 140-B and then bonding or otherwise attaching the high-transmissive substrates 140-A, 140-B.

Figure 6:
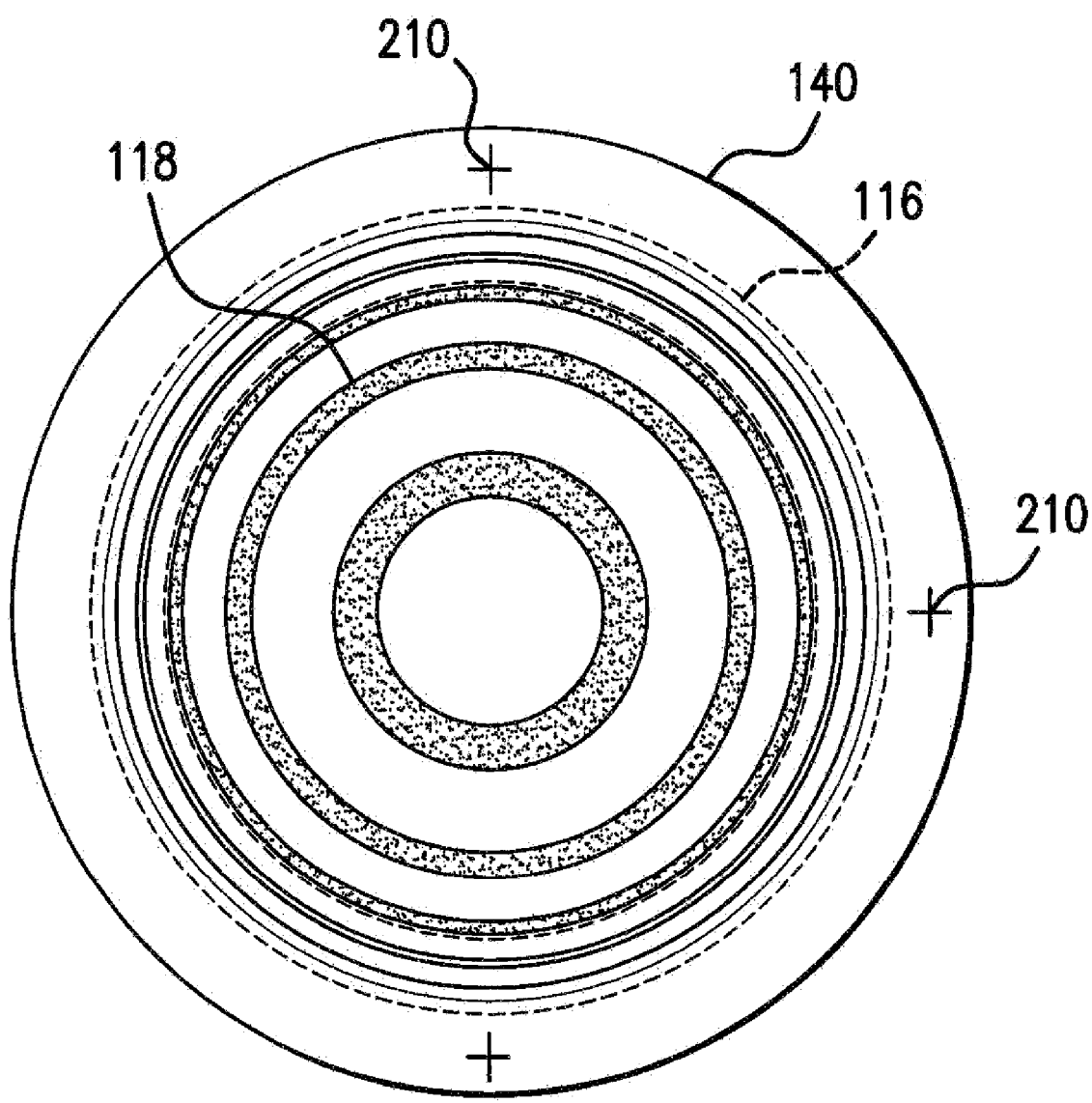
FIG. 6 is a plan view of a composite optic showing alignment fiducials according to the present invention.

As shown in FIG. 6, the alignment between the objective 118 and the phase plate 116 is accomplished, in the preferred embodiment, by including alignment fiducials 210 on the high-transmissive substrate or high-transmissive substrates 140 of the phase plate 116 and the zone plate objective 118. In the situation where the phase plate and zone plate are fabricated on the same high-transmissive substrate, the alignment fiducials are used during the lithographic patterning steps. If the phase plate 116 and zone plate 118 are fabricated on opposed sides of the high-transmissive substrate 140, the high-transmissive substrate 140 is either thinned such that the fiducials are discernable from the backside or transferred to the backside in a frontside/backside alignment process.

Figure 7:
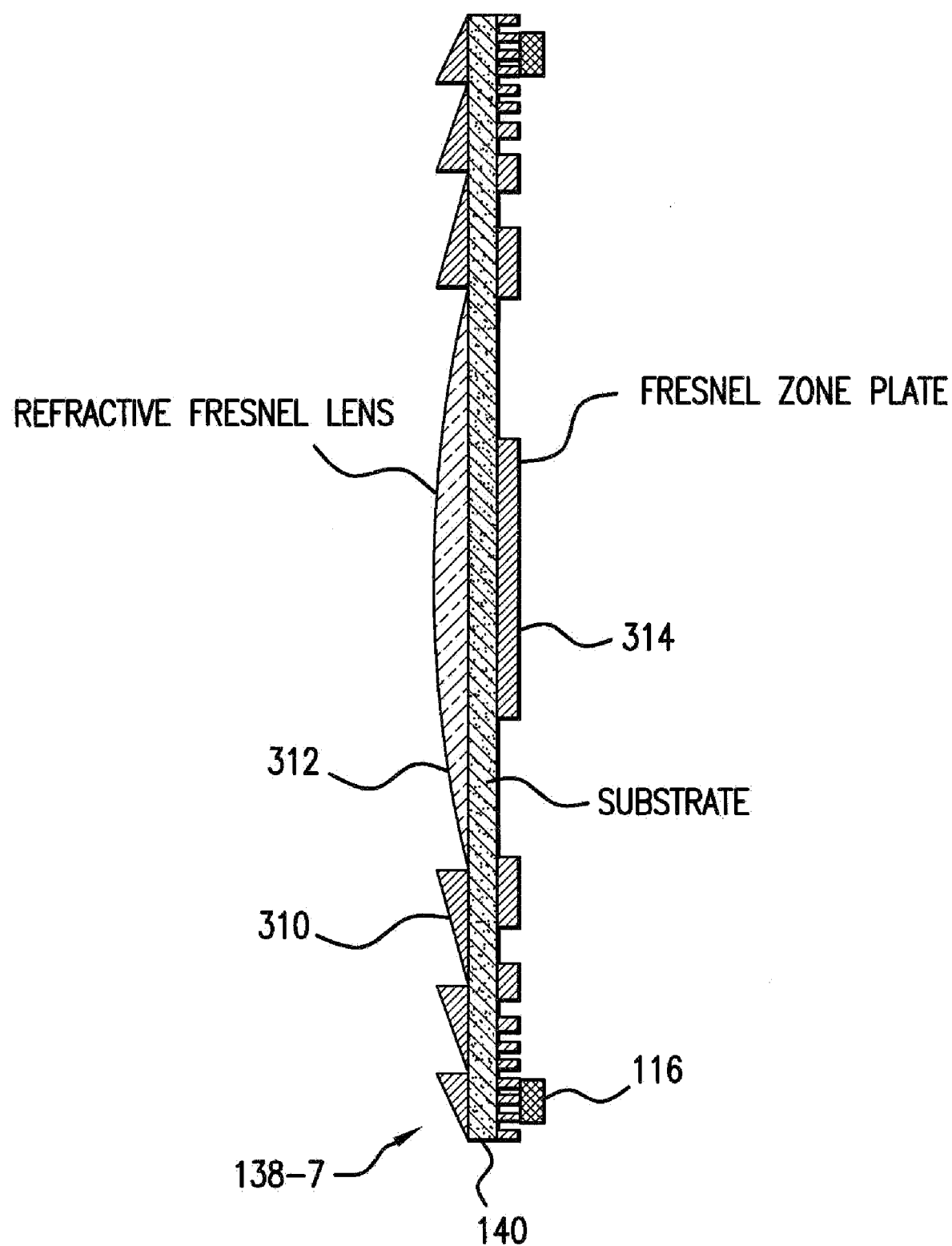
FIG. 7 is a cross-sectional view of composite optic comprising an achromatic Fresnel optic (AFO) and a phase plate according to still another embodiment.

FIG. 7 shows still another implementation of the composite optic. Here, the composite optic 138-7 is a combination of a phase plate 116 and an objective, which is an achromatic Fresnel optic (AFO) 310. The configuration of the AFO 310 is preferably as described in U.S. patent application Ser. No. 10/134,026, which application is incorporated herein in its entirety by this reference. Specifically, the AFO 310 is a combination of a Fresnel refractive lens 312 and a zone plate 314. In the illustrated embodiment, the phase plate 116 is fabricated on the zone plate 314, which is fabricated on a substrate 140. The Fresnel lens 312 is fabricated on the other side of the substrate 140.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for fabricating a composite optic, comprising:
   forming fiducials on a substrate;
   forming an objective on the substrate;
   forming a phase plate on the substrate and on an opposite side of the substrate from the objective; and
   aligning the phase plate relative to the objective using the fiducials.

2. A method as claimed in claim 1, wherein the step of forming the phase plate comprises forming a phase ring.

3. A method as claimed in claim 1, wherein the step of forming the objective comprises forming a zone plate.

4. A method as claimed in claim 1, wherein the step of forming the objective comprises forming a Fresnel lens.

5. A method as claimed in claim 1, wherein the substrate is curved in the direction of a test object.

6. A method for fabricating a composite optic, comprising:
forming fiducials on a substrate, wherein the substrate is curved in the direction of a test object;
forming an objective on the substrate;
forming a phase plate on the substrate;
aligning the phase plate relative to the objective using the fiducials.

7. A method as claimed in claim 6, wherein the step of forming the objective comprises forming a zone plate.

8. A method as claimed in claim 6, wherein the step of forming the objective comprises forming a Fresnel lens.

9. A method as claimed in claim 6, further comprising forming the objective and the phase plate on opposite sides of the substrate.

10. A method as claimed in claim 6, wherein the step of forming the phase plate comprises forming a phase ring.

11. A method for fabricating a composite optic, comprising:
forming fiducials on a substrate;
forming an objective on the substrate;
forming a phase ring on the substrate; and
aligning the phase ring relative to the objective using the fiducials.

12. A method as claimed in claim 11, further comprising forming the phase ring on top of the objective.

13. A method as claimed in claim 11, wherein the step of forming the objective comprises forming a zone plate.

14. A method as claimed in claim 11, wherein the step of forming the objective comprises forming a Fresnel lens.

15. A method as claimed in claim 11, further comprising forming the phase ring on top of the objective.

16. A method as claimed in claim 11, wherein the substrate is curved in the direction of a test object.

17. A method as claimed in claim 11, further comprising forming the objective and the phase ring on opposite sides of the substrate.

* * * * *